(12) United States Patent
Sanchez et al.

(10) Patent No.: US 7,780,446 B2
(45) Date of Patent: Aug. 24, 2010

(54) CERAMIC/METALLIC DENTAL ABUTMENT

(75) Inventors: Ramiro Sanchez, Temecula, CA (US); Christopher M. Gervais, San Marcos, CA (US); Jeff A. Bassett, Vista, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

(21) Appl. No.: 11/362,236

(22) Filed: Feb. 24, 2006

(65) Prior Publication Data
US 2007/0202463 A1 Aug. 30, 2007

(51) Int. Cl.
*A61C 8/00* (2006.01)
(52) U.S. Cl. .................................. 433/173
(58) Field of Classification Search ............... 433/173, 433/172, 174, 175, 176, 201.1, 202.1, 215, 433/220, 221
See application file for complete search history.

(56) References Cited

U.S. PATENT DOCUMENTS

| 4,872,839 | A |   | 10/1989 | Brajnovic |         |
|-----------|---|---|---------|-----------|---------|
| 5,030,095 | A | * | 7/1991  | Niznick   | 433/173 |
| 5,125,839 | A |   | 6/1992  | Ingber et al. |    |
| 5,281,140 | A | * | 1/1994  | Niznick   | 433/172 |
| 5,447,434 | A | * | 9/1995  | Shaw      | 433/173 |
| 5,571,016 | A |   | 11/1996 | Ingber et al. |    |
| 5,685,714 | A |   | 11/1997 | Beaty et al. |     |
| 5,947,732 | A |   | 9/1999  | Beaty et al. |     |
| 5,989,026 | A |   | 11/1999 | Rogers et al. |    |
| 6,152,737 | A |   | 11/2000 | Beaty et al. |     |
| 6,168,435 | B1|   | 1/2001  | Beaty et al. |     |
| RE37,227  | E |   | 6/2001  | Brodbeck  |         |
| 6,343,930 | B1|   | 2/2002  | Beaty et al. |     |
| 2004/0101807 | A1 | * | 5/2004 | Porter et al. | 433/173 |
| 2004/0185417 | A1 | * | 9/2004 | Rassoli      | 433/173 |
| 2004/0234926 | A1 | * | 11/2004| Halldin et al. | 433/173 |
| 2005/0014108 | A1 | * | 1/2005 | Wohrle et al. | 433/173 |
| 2005/0136378 | A1 | * | 6/2005 | Ennajimi et al. | 433/173 |
| 2006/0105296 | A1 |   | 5/2006 | Linder et al. |         |

FOREIGN PATENT DOCUMENTS

| DE | 201 10 768 U1 | 11/2002 |
| WO | WO97/10770    | 3/1997  |
| WO | WO 00/24335   | 5/2000  |

OTHER PUBLICATIONS

International Search Report from PCT/US2007/016819 Mailed Jul. 24, 2007.

* cited by examiner

*Primary Examiner*—Cris L Rodriguez
*Assistant Examiner*—Heidi M Eide
(74) *Attorney, Agent, or Firm*—Fitch, Even, Tabin & Flannery

(57) ABSTRACT

A ceramic/metallic dental abutment for use with an implant, the abutment generally including a ceramic body portion having a base region, a transgingival region, and a supragingival region. The base region includes an anti-rotational implant interface, such as an external polygonal fitting, for engaging a cooperating internal polygonal fitting of an implant to prevent relative rotation between the abutment and the implant. The ceramic abutment body portion additionally includes a metal implant contact portion for contacting the implant and providing a load-bearing, metal-on-metal interface between the abutment and the implant.

15 Claims, 4 Drawing Sheets

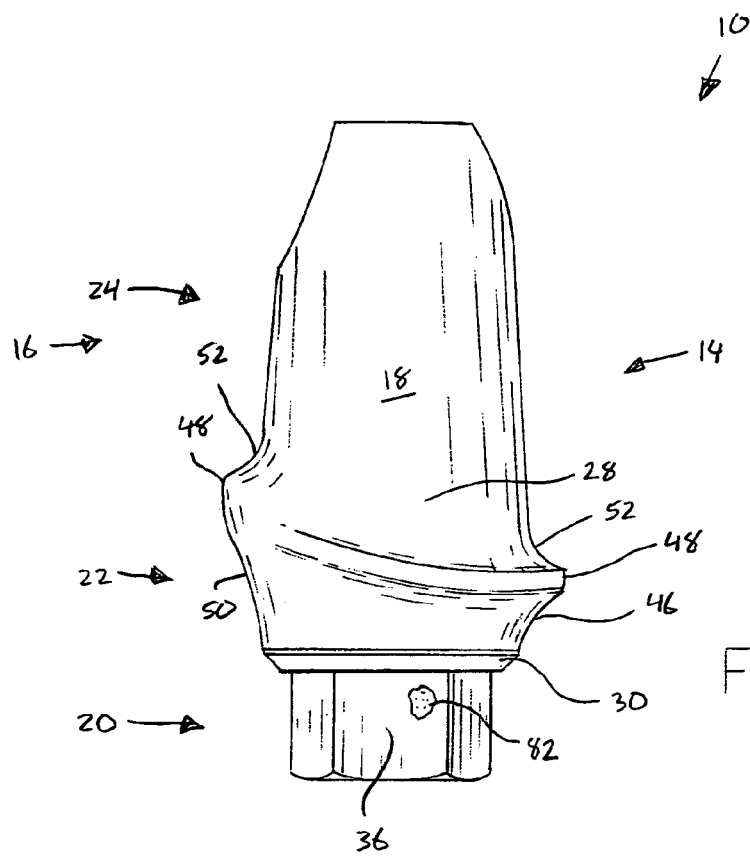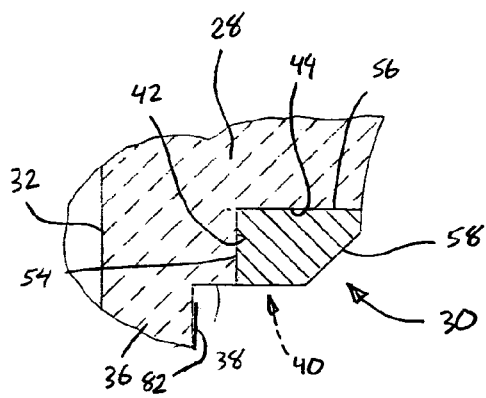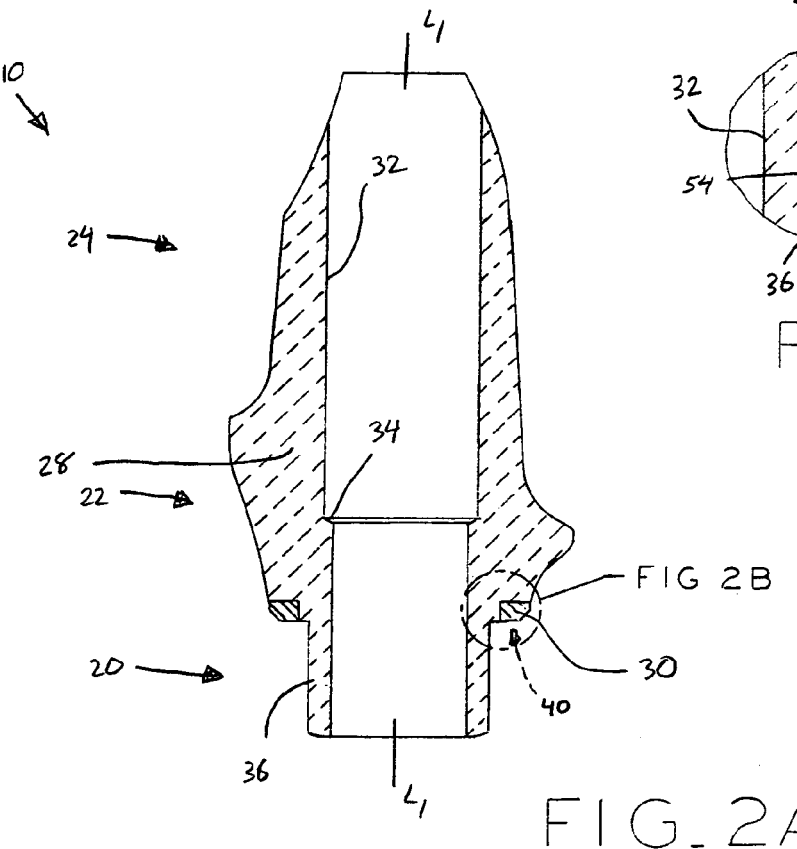

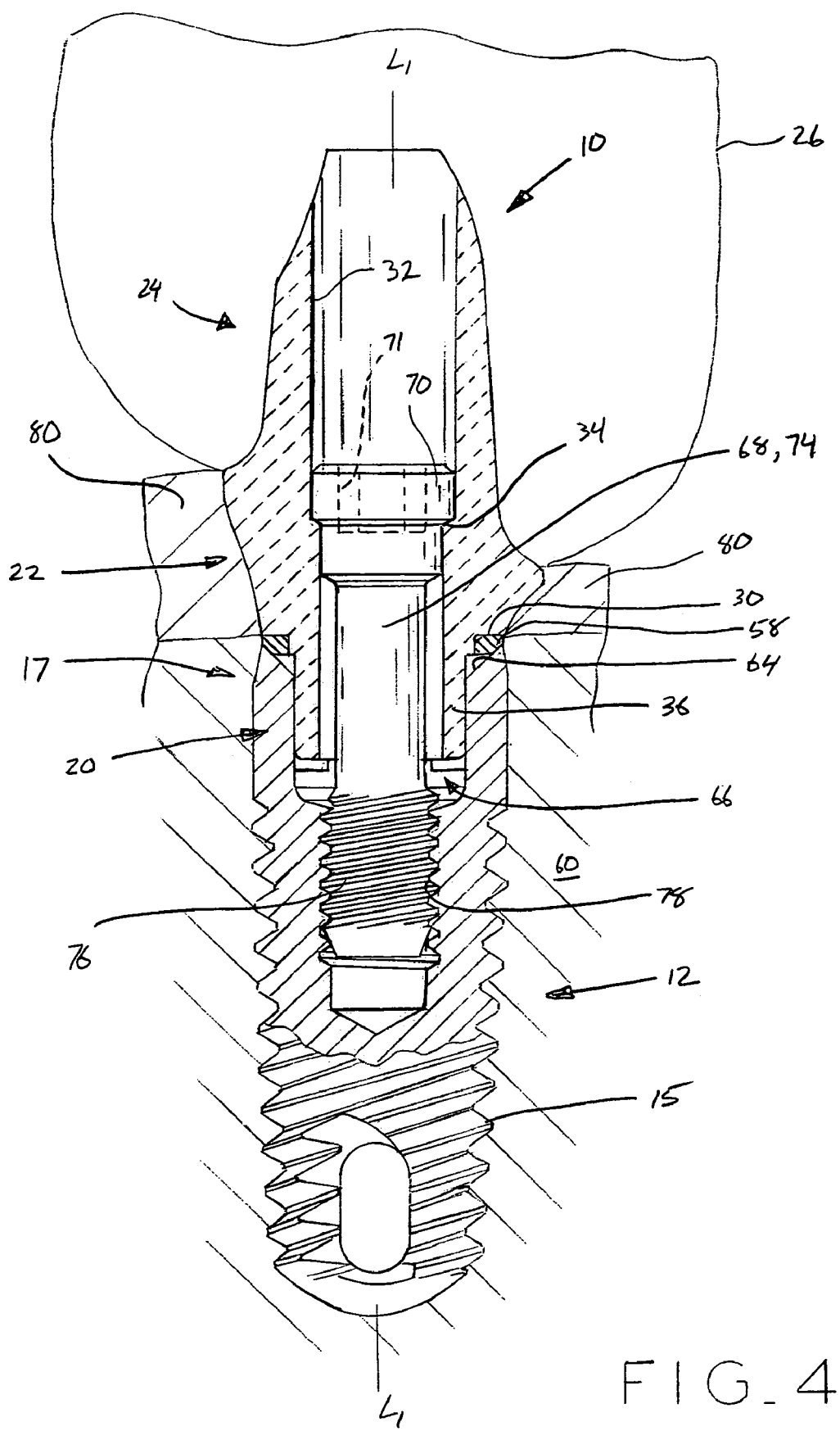
FIG_4

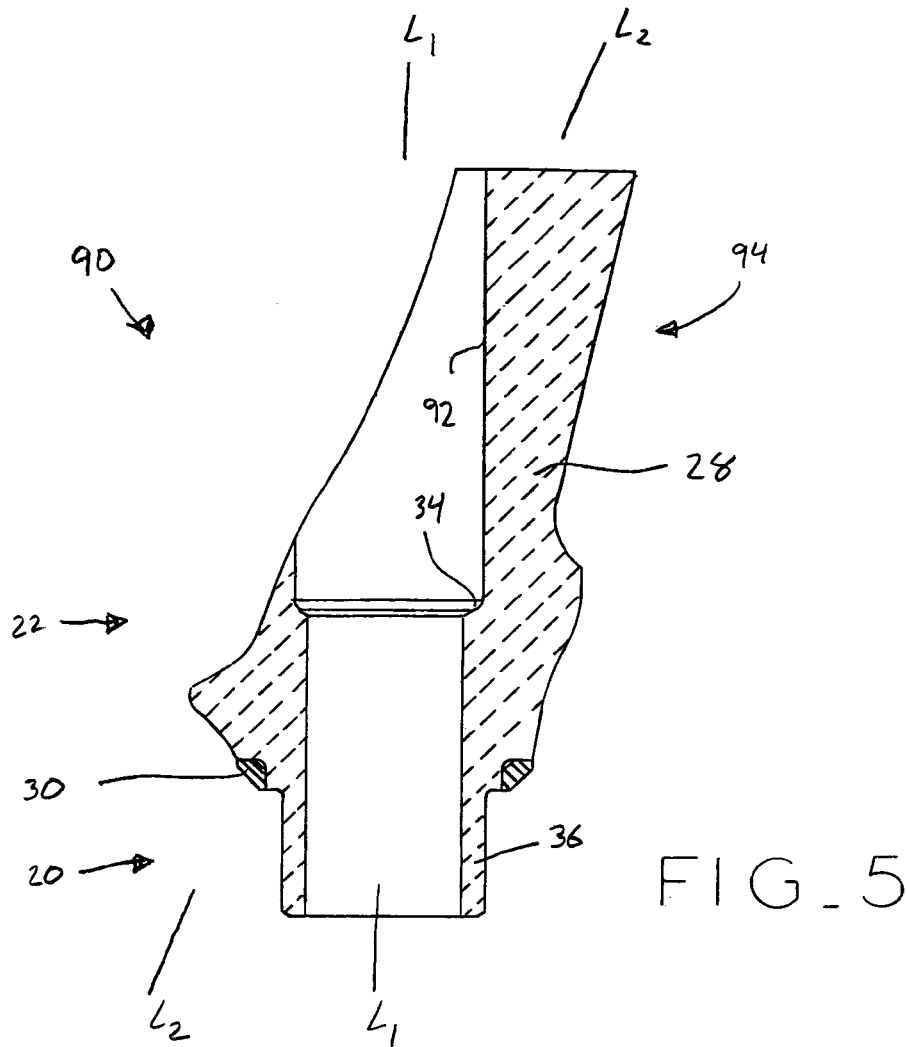
FIG_5
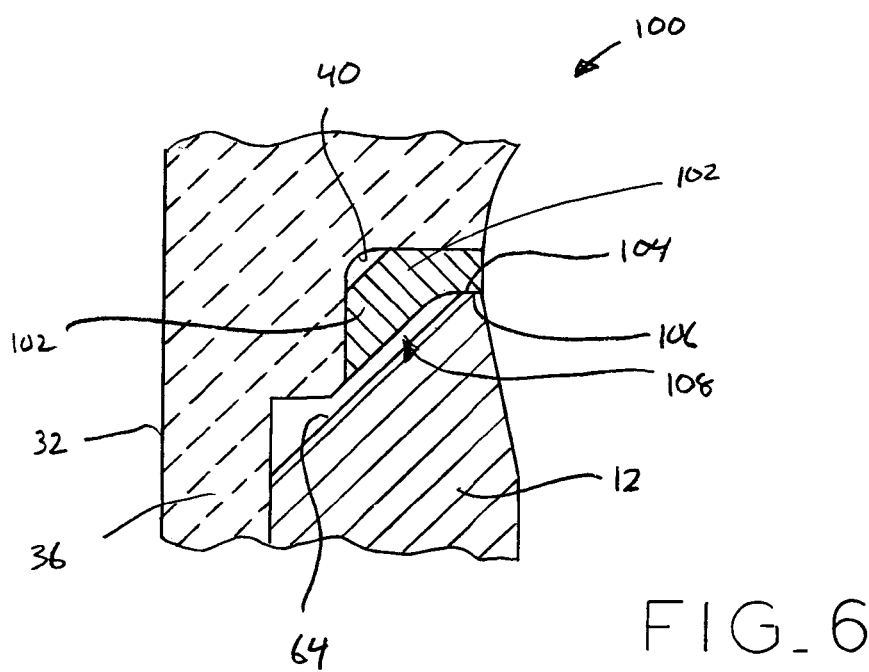
FIG_6

CERAMIC/METALLIC DENTAL ABUTMENT

BACKGROUND OF THE INVENTION

1. Field of the Invention

The present invention relates to dental prosthetics and, in particular, to a ceramic/metallic abutment for use with a dental implant as part of a prosthodontic restoration.

2. Description of the Related Art

Dental implants are commonly used as anchoring members in prosthodontic restorations to provide prosthetic teeth at one or more edentulous sites in a patient's dentition at which the patient's original natural teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods to replicate the shape of the tooth being replaced.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist surgically reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example.

Typically, abutments are made from a biocompatible metal, such as titanium, or from a ceramic material. Advantages of titanium abutments include structural strength and relative ease of manufacture. However, if recession of the gingival tissue occurs around the implant and abutment after implantation, there is the potential that a portion of the metal of the abutment beneath the crown may become exposed, such that the grey color of the titanium is visible, which is aesthetically disadvantageous.

Ceramic abutments are harder than titanium abutments, and have the additional advantage of providing a light, tooth-like color such that, in the event of gingival recession, the light color of any exposed portions of the abutment substantially match the color of the crown and appear tooth-like to preserve aesthetics.

What is needed is an abutment which is an improvement over the foregoing.

SUMMARY OF THE INVENTION

The present invention provides a ceramic/metallic dental abutment for use with an implant, the abutment generally including a ceramic body portion having a base region, a transgingival region, and a supragingival region. The base region includes an anti-rotational implant interface, such as an external polygonal fitting, for engaging a cooperating internal polygonal fitting of an implant to prevent relative rotation between the abutment and the implant. The ceramic abutment body portion additionally includes a metal implant contact portion for contacting the implant and providing a load-bearing, metal-on-metal interface between the abutment and the implant.

In one embodiment, the implant contact portion is provided in the form of an annular metal ring made of titanium, for example, which is attached to the abutment via a press-fit connection, an adhesive connection, a shrink-fit connection, a brazed connection, or in another suitable manner. The implant contact portion is disposed substantially at the interface between the base region and the transgingival region of the abutment, and is dimensioned such that, when the abutment is connected to the implant, the implant contact portion is substantially entirely contained within the outer periphery of the open proximal end of the implant. Therefore, after attachment of the abutment to the implant, the implant contact portion is not visible and does not contact soft tissue surrounding the abutment.

In one embodiment, the proximal end of the implant includes an annular chamfer disposed at an oblique angle with respect to the longitudinal axis of the implant and abutment, and the implant contact portion of the abutment includes a contact surface disposed at a cooperating angle for engagement with the implant chamfer. The internal polygonal fitting of the implant may be greater in length than the external polygonal fitting of the abutment such that, upon receipt of the external polygonal abutment fitting into the internal polygonal implant fitting, relative rotation between the abutment and implant is prevented while axial loads from the abutment, such as occlusal and/or mastication loads, for example, are transferred to the implant only through the implant contact portion for improved resistance to wear.

In one form thereof, the present invention provides a dental abutment, including a ceramic body portion defining a longitudinal axis, and including a base region with an anti-rotational implant interface, a transgingival region, and a supragingival region; a bore extending through the body portion along the longitudinal axis; and a metal implant contact portion attached to the body portion and disposed adjacent the implant interface.

In another form thereof, the present invention provides a dental abutment, including a ceramic body portion having a longitudinal axis, a bore extending through the body portion along the longitudinal axis, and an anti-rotational implant interface; and metal implant contact means attached to the body portion for axial load-bearing contact with an implant.

In a further form thereof, the present invention provides, in combination, a dental implant, including an externally threaded body having a distal end and a proximal end; a bore extending into the proximal end, the bore including a threaded portion and a first anti-rotational interface; and a dental abutment, including a ceramic body portion including a second anti-rotational interface cooperable with the first anti-rotational interface of the implant whereby relative rotation between the abutment and the implant is prevented; and a metal contact portion abuttable with the proximal end of the implant.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is a perspective, interproximal view of a ceramic/metallic abutment in accordance with the present invention;

FIG. 2A is a sectional view of the abutment of FIG. 1;

FIG. 2B is a fragmentary view of a portion of FIG. 2A;

FIG. 4 is a sectional view of the implant, abutment, and abutment screw of FIG. 3, with the implant implanted within a jawbone and a crown secured to the abutment;

FIG. 5 is a sectional view of an angled abutment according to a further embodiment; and FIG. 6 is an enlarged fragmentary view of a portion of an abutment according to another embodiment.

Corresponding reference characters indicate corresponding parts throughout the several views. The exemplifications set out herein illustrate preferred embodiments of the invention, and such exemplifications are not to be construed as limiting the scope of the invention any manner.

DETAILED DESCRIPTION

Figure 3:
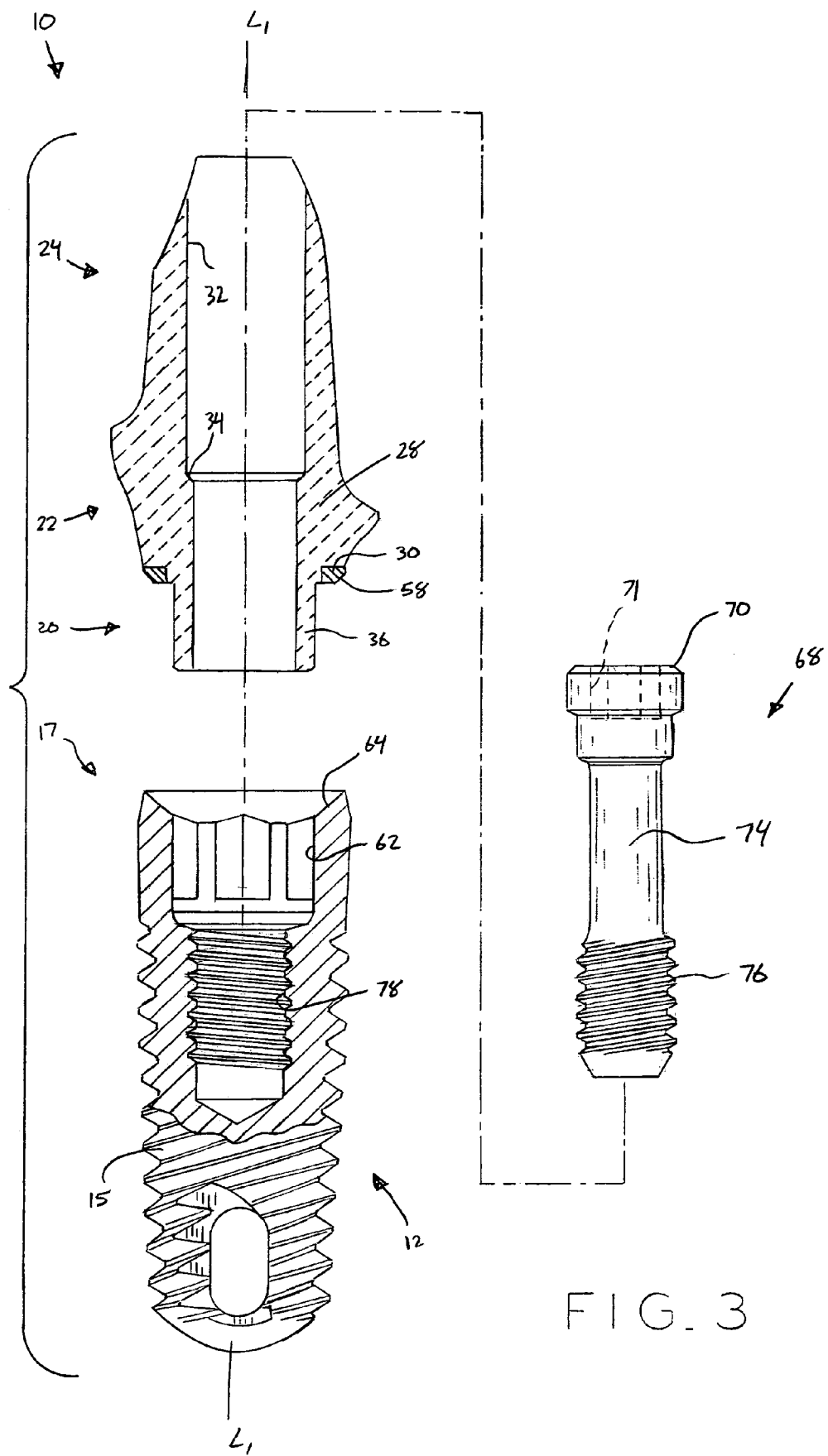
FIG. 3 is a sectional, exploded view showing the abutment together with an implant and an abutment screw.

Referring first to FIGS. 1, 2A, and 2B, a ceramic/metallic dental abutment 10 according to the present invention is shown, which may be used with a dental implant 12, such as that shown in FIGS. 3 and 4 and described below, to provide a prosthetic tooth at an edentulous site in a patient's dentition at which a natural tooth has been lost or damaged. In FIG. 1, an interproximal view of abutment 10 is shown, which includes a facial side 14 and an opposing lingual side 16, as well as a mesial side 18 and an opposing distal side (not visible in FIG. 1). Abutment 10 also generally includes a base region 20 for interfacing with implant 12, an emergence profile region or transgingival region 22 which extends through soft gingival tissue, and a coronal region or supragingival region 24 extending superiorly of transgingival region 22 to which a prosthetic tooth or crown 26 may be attached, as shown in FIG. 4.

Abutment 10 includes a body portion 28 made of a suitable ceramic material, such as aluminum oxide or zirconium oxide, for example, and body portion 28 additionally includes an implant contact portion 30, described below, which may be made of a suitable biocompatible metal, such as titanium, for example. As shown in FIG. 2A, body portion 28 of abutment 10 includes a central bore 32 therethrough extending along the longitudinal axis $L_1$-$L_1$ of abutment 10, with bore 32 including step 34 for abutting engagement by the head of an abutment screw to secure abutment 10 to implant 12 in the manner described below. Although transgingival region 22 and supragingival region 24 of abutment 10 extend substantially along the direction of longitudinal axis $L_1$-$L_1$ in the embodiment shown in FIGS. 1-4, in other embodiments, transgingival region 22 and/or supragingival region 24 of abutment 10 may be angled away from bore 32 and longitudinal axis $L_1$-$L_1$ as needed to conform to the anatomical orientation of the tooth being replaced.

For example, referring to FIG. 5, an angled abutment 90 is shown which, except as described below, is substantially identical to abutment 10, and the same reference numerals are used to designate identical features therebetween. In abutment 90, central bore 92 thereof is disposed along central longitudinal axis $L_1$-$L_1$ of abutment 90, while supragingival region 94 of abutment 90 is oriented or disposed along an axis $L_2$-$L_2$ which angled with respect to central bore 94 and longitudinal axis $L_1$-$L_1$.

Base region 20 of abutment 10 includes an implant interface, shown herein as an external polygonal fitting 36 having a hexagonal shape. In other embodiments, abutment 10 could include an internal polygonal fitting and/or a polygonal fitting which includes more or less than six sides. Referring additionally to FIG. 2B, at its upper end adjacent transgingival region 22, polygonal fitting 36 terminates at shelf 38 adjacent a notch 40 disposed substantially at the transition of base region 20 and transgingival region 22, with notch 40 including annular rim 42 and annular base wall 44 within which implant contact portion 30 is fitted, as described below.

Referring to FIG. 1, transgingival region 22 of abutment 10 includes concave surface 46 extending toward margin shoulder 48 of transgingival region 22 on facial side 14 of abutment 10, and another concave surface 50 extending toward margin shoulder 48 on lingual side 16 of abutment 10. Margin shoulder 48 is disposed substantially at the gingival or gum line, is contoured to follow the gingival line based on the anatomy of the tooth being replaced, and includes concave recesses 52 on each of its sides which merge into the outer profile of supragingival region 24.

Referring to FIGS. 1, 2A, and 2B, abutment body portion 28 additionally includes an implant contact portion 30, shown herein in the form of an annular metal ring, for example. Implant contact portion 30 may be made of substantially the same material as implant 12, such as a suitable biocompatible metal, for example, titanium. As best shown in FIG. 2B, implant contact portion 30 generally includes annular inner surface 54 and annular top surface 56 disposed against rim 42 and base wall 44 of notch 40 of abutment body portion 28, respectively, as well as an implant contact surface 58 disposed at an oblique angle with respect to longitudinal axis $L_1$-$L_1$ of abutment 10, which surface contacts implant 12 in the manner described below.

Implant contact portion 30 may be attached to abutment body portion 28 via a press-fit connection, in which implant contact portion 30 is pressed with force onto rim 42 and against base wall 44 within notch 40 to firmly retain same on body portion 28 of abutment 10; an adhesive connection, in which a suitable adhesive or cement is applied between notch 40 and implant contact portion 30 which, when cured, firmly secures implant contact portion 30 to abutment body portion 28 within notch 40; a shrink-fit connection, in which implant contact portion 30 is heated, pressed onto rim 42 against base wall 44 within notch 40, and is then cooled to shrink the diameter of implant contact portion 30 slightly such that same is firmly retained to abutment body portion 28; or a brazed connection, in which implant contact portion 30 is pressed around rim 42 against base wall 44 within notch 40 and is then heat brazed to body portion 28.

Referring to FIGS. 3 and 4, implant 12 includes a threaded body 15 which is implanted into a tapped bore in the jawbone 60 (FIG. 4) of a patient according to known surgical techniques. After implant 12 is allowed to osseointegrate within jawbone 60, abutment 10 is initially seated on implant 12 by inserting external polygonal fitting 36 of abutment 10 into an internal polygonal fitting 62 of implant 12. Also, when abutment 10 is seated on implant 12, implant contact portion 30 of abutment 10 engages an internal annular chamfer 64 at the proximal end 17 of implant 12. Implant contact surface 58 of implant contact portion 30 of abutment 10 and chamfer 64 of implant 12 are complementary angled at an oblique angle relative to longitudinal axis $L_1$-$L_1$ of abutment 10 and implant 12.

As may be seen in FIG. 4, external polygonal fitting 36 of abutment 10 is slightly shorter along the direction of longitudinal axis $L_1$-$L_1$ of abutment 10 and implant 12 than internal polygonal fitting 60 of implant 12, such that an axial clearance space 66 is provided within internal polygonal fitting 62 of implant 12 distally of external polygonal fitting 36 of abutment 10. In this manner, the engagement between external polygonal fitting 36 of abutment 10 and internal polygonal fitting 60 of implant 12 prevents rotation of abutment 10 with respect to implant 12 without supporting the weight of abutment 10 and crown 26 or bearing loads along the direction of longitudinal axis $L_1$-$L_1$ of abutment 10. Rather, the metal-on-metal contact between implant contact portion 30 of abutment 10 and chamfer 64 of implant 12 supports the weight of abutment 10 and crown 26, as well as loads imposed upon abutment 10 and crown 26 along or divergent from the direction of longitudinal axis $L_1$-$L_1$ of abutment 10, such as occlusal and/or mastication loads, for example.

An abutment screw 68, shown in FIG. 3, is provided for securing abutment 10 to implant 12, and generally includes head 70 with instrument engagement structure such as an internal polygonal fitting 71, for example, as well as shank portion 74 extending from head 70 and having threads 76 thereon distally of head 70. In use, abutment screw 68 is inserted through central bore 32 of abutment 10, and threads 76 of abutment screw 68 are threaded into internally threaded region 78 of implant 12 with head 70 of abutment screw 68 initially seating against step 34 within internal bore 32 of abutment 10.

Thereafter, further tightening of abutment screw 68 presses head 70 thereof against seat 34 to firmly engage abutment 10 to implant 12 and, more specifically, to firmly press implant contact portion 30 of abutment 10 into engagement with chamfer 64 of implant 12, such that the loads imposed via abutment screw 68 along the direction of longitudinal axis $L_1$-$L_1$ of abutment 10 are transferred to implant 12 directly through implant contact portion 30. The firm engagement between implant contact portion 30 of abutment 10 and chamfer 64 of implant 12 minimizes micromotion between abutment 10 and implant 12.

After abutment screw 68 is tightened, abutment 10 is securely retained to implant 12 via the engagement of implant contact portion 30 of abutment 10 with chamfer 64 of implant 12, wherein a small gap may be present between external polygonal fitting 36 of abutment 10 and internal polygonal fitting 60 of implant 12 such that direct contact between the ceramic material of external polygonal fitting 36 of abutment 10 and the metal of internal polygonal fitting 60 of implant 12 is minimized. Advantageously, the metal-on-metal contact between implant contact portion 30 and implant 12 provides increased resistance to wear therebetween, due to the similarity or identity of the materials of implant contact portion 30 and implant 12.

After abutment 10 is secured to implant 12 in the manner described above, crown 26 may be attached to supragingival region 24 of abutment 10 via cement, for example, to complete the restoration. Advantageously, as can be seen in FIGS. 3 and 4, implant contact portion 30 of abutment 10 is disposed within the open proximal end 17 of implant 12. In one alternative form, the implant contact portion 30 is disposed substantially entirely within the open proximal end 17 such that implant contact portion 30 is not visible externally of the prosthetic and, in the event of recession of gingival tissue 80 around transgingival region 22 of abutment 10, implant contact portion 30 will not be visible. Further, receipt of implant contact portion 30 substantially entirely within the open proximal end 17 of implant 12 prevents the metal of implant contact portion 30 from contacting the soft gingival tissue 80 around abutment 10 and implant 12.

As shown in part in FIGS. 1 and 2B, ceramic body portion 28 and/or implant contact portion 20, in the area of base region 20 and/or transgingival region 22 of abutment 10, may be coated with a thin coating 82 of gold or other metallic or non-metallic coating, such as by electroplating or sputtering techniques, for example, such as for providing a light, tooth-like coloring for aesthetics.

Referring to FIG. 6, a portion of an abutment 100 according to another embodiment is shown which, except as described below, is identical to abutment 10 described above, and the same reference numerals are used to indicate identical or substantially identical features therebetween. Abutment 100 includes contact portion 102 similar to contact portion 30 described above, and which may be attached to abutment 100 in the same manner as contact portion 30 is attached to abutment 10. Contact portion 102 includes an annular outer end surface 104 dimensioned to seat on a proximal, outer annular rim 106 of implant 12, which a small clearance space 108 present between contact portion 102 and chamfer 64 of implant 12, wherein load are transferred from abutment 100 to implant 12 via outer end surface 104 of contact portion 102 to the proximal, outer annular rim 106 of implant 12.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. In combination:
  a dental implant, comprising:
    an externally threaded body having a distal end and a proximal end, said proximal end including a first anti-rotational interface and a threaded portion;
  a dental abutment, comprising:
    a ceramic body portion defining a longitudinal axis, and including a base with a second anti-rotational interface cooperable with said first anti-rotational interface of said implant whereby relative rotation between said abutment and said implant is prevented;
    a metal contact portion that is other than an anti-rotational interface and comprising at least two transversely spaced portions relative to the longitudinal axis, the base extending directly between the at least two transversely spaced portions for extending toward the implant, the metal contact portion being abuttable with said proximal end of said implant; and
  a screw configured for threadedly connecting the dental implant to the dental abutment and configured for engaging a screw seating surface on the dental abutment,
    wherein said implant includes a chamfer disposed at an oblique angle with respect to said axis; and
    wherein said metal contact portion includes a contact surface configured to engage said chamfer, and an inner portion disposed radially inward from the contact surface and extending over the chamfer so that a space is maintained between the metal contact portion and the chamfer, said ceramic body being substantially longitudinally supported at said chamfer.

2. The combination of claim 1, wherein said implant has an implant bore for receiving the abutment, and wherein said metal contact portion is substantially entirely received within said implant bore when said abutment is attached to said implant.

3. The combination of claim 1, wherein said first anti-rotational interface comprises an internal polygonal fitting and said second anti-rotational interface comprises an external polygonal fitting.

4. The combination of claim 3, wherein said internal polygonal fitting has a length greater than a length of said external polygonal fitting, whereby axial loads from said abutment are transferred to said implant substantially only via said metal contact portion.

5. The combination of claim 1, wherein said metal contact portion is disposed at least in part adjacent a transgingival portion of said abutment.

6. The combination of claim 1, wherein said metal contact portion is attached to said ceramic body portion in a manner selected from the group consisting of a press-fit connection, an adhesive connection, a shrink-fit connection, and a brazed connection.

7. The combination of claim 1, wherein said abutment includes a transgingival region, at least a portion of said transgingival region oriented along an axis which is angled with respect to said longitudinal axis.

8. The combination of claim 1, wherein the second anti-rotational implant interface of the base is disposed in direct contact with the dental implant for forming an anti-rotational connection.

9. The combination of claim 1, wherein the second anti-rotational interface is radially spaced from the metal contact portion.

10. The combination of claim 1, wherein the metal contact portion defines a through-bore, and wherein the base extends through the through-bore.

11. The combination of claim 1, wherein the metal contact portion comprises a ring defining a main through-bore, and wherein the base extends through the through-bore.

12. The combination of claim 1 wherein the implant has a coronal opening, and wherein the metal contact portion is disposed substantially entirely within the coronal opening.

13. The combination of claim 1 wherein the chamfer has a radial width, and wherein the contact surface contacts less than the entire radial width of the chamfer.

14. A dental device generally defining a longitudinal axis and comprising:
   a dental implant having a coronal end forming a coronal opening with a chamfer surface extending at an oblique angle relative to the longitudinal axis; and
   an abutment for attachment to the coronal end of the implant, the abutment comprising:
      a ceramic body forming an anti-rotational connection with the implant, and
      a metal contact portion that is other than an anti-rotational connection and having a contact surface for engaging the implant and a lower surface disposed radially inward from the contact surface,
      the lower surface extending generally at the oblique angle and generally parallel to the chamfer surface,
      the lower surface being disposed to directly face the chamfer surface while maintaining a space between the lower surface and the chamfer surface,
   wherein the metal contact portion is a ring with an outer portion extending substantially perpendicular to the longitudinal axis and forming the contact surface, the metal contact portion further comprising an annular conical wall extending apically as the conical wall extends radially inward from the outer portion, wherein the conical wall forms the lower surface.

15. The device of claim 14 wherein the dental implant further comprises a coronal rim extending radially outward from the chamfer, and wherein the contact surface engages the rim for longitudinally supporting the ceramic body.

* * * * *